United States Patent [19]
Lin

[11] Patent Number: 6,068,597
[45] Date of Patent: May 30, 2000

[54] VIBRATIONAL RESONANCE ULTRASONIC DOPPLER SPECTROMETER AND IMAGER

[76] Inventor: Gregory Sharat Lin, 33808 Cassio Cir., Fremont, Calif. 94555-2016

[21] Appl. No.: 09/290,933

[22] Filed: Apr. 13, 1999

[51] Int. Cl.⁷ .................................................. A61B 8/00
[52] U.S. Cl. .......................... 600/443; 600/459; 73/579; 73/584
[58] Field of Search .................... 600/561, 587, 600/438, 443, 437, 459; 73/579, 584, 598

[56] References Cited

U.S. PATENT DOCUMENTS

| | | | |
|---|---|---|---|
| 5,099,848 | 3/1992 | Parker et al. | 600/441 X |
| 5,810,731 | 9/1998 | Sarvazyan et al. | 600/438 |
| 5,855,557 | 6/1999 | Lazenby | 600/443 |
| 5,919,139 | 7/1999 | Lin | 600/443 |
| 5,997,477 | 12/1999 | Schgol | 600/437 |

OTHER PUBLICATIONS

Lin, G.S. et al "Differentiation of Benign Versus Malignant breast masses with vibrational resonance ultrasonic Doppler Spectroscopy", Eur. Jral Ultrasound vol. 10 suppl. Sep. 1, 1999 p. 517.

U.S. Application No. 08/993,337, G. S. Lin.

K. J. Parker et al., "Tissue Response to Mechanical Vibrations for 'Sonoelasticity Imaging'". Ultrasound in Med. & Biol., vol. 16, No. 3 (1990) pp. 241–246.

L. Gao et al., "Imaging of the Elastic Properties of Tissue—A Review". Ultrasound in Med. & Biol., vol. 22, No. 8 (1996) pp. 959–977.

*Primary Examiner*—Francis J. Jaworski

[57] ABSTRACT

A system is disclosed for performing vibrational resonance ultrasonic Doppler spectrometry to produce characteristic vibrational resonance spectra of soft structures in compressible media or soft tissues in a living body. A system is further disclosed for vibrational resonance ultrasonic Doppler imaging of the spatial distribution of vibrational resonance properties. An audio-frequency source externally applies a sequence of vibrational frequencies into a medium or body. Ultrasonic pulsed Doppler beams are focused at various locations within a region of interest, and the received Doppler signals are used to estimate the amplitude of the vibrational resonance response at each location. A vibrational resonance spectrum is computed from received Doppler amplitudes at each vibrational frequency and graphically displayed. Mapping the vibrational resonance spectra of a plurality of regions of interest into colors and brightness according to specific curve shape criteria further generates a two-dimensional vibrational resonance image. These methods may be utilized in the detection and differentiation of tumors of the breast, prostate, liver, and other soft tissues.

19 Claims, 11 Drawing Sheets

| Ratio of peaks: | $\dfrac{A_c}{A_a}$ | ⟶ Red |
| Upper sideband width: | $f_{c+} - f_c$ | ⟶ Green |
| Peak-valley ratio: | $\dfrac{A_c}{A_b}$ | ⟶ Blue |
| Number of peaks | ⟶ | Brightness |

VIBRATIONAL RESONANCE ULTRASONIC DOPPLER SPECTROMETER AND IMAGER

FIELD OF THE INVENTION

The present invention generally relates to ultrasonic imaging, and more specifically to characterizing and imaging the vibrational resonance properties of complex compressible media and biological tissues with power Doppler ultrasound.

BACKGROUND OF THE INVENTION

Ultrasonic imaging technology has become an important tool for examining the internal structure of living organisms. In the diagnosis of various medical conditions, ultrasonic imaging is often useful to examine soft tissues within the body to show the structural detail of internal tissues and fluid flow. An important application of ultrasonic imaging is in the detection and identification of various internal structural abnormalities, such as cysts, tumors, abcesses, mineral deposits, blood vessel obstructions, and anatomical defects without physically penetrating the skin.

Ultrasonic images are formed by producing very short pulses of ultrasound using an electro-acoustic transducer, sending the pulses through the body, and measuring the properties (e.g., amplitude and phase) of the echoes from tissues within the body. Focused ultrasound pulses, referred to as "ultrasound beams", are targeted to specific tissue regions of interest in the body. Typically, an ultrasound beam is focused at small lateral and depth intervals within the body to improve spatial resolution. Echoes are received by the ultrasound transducer and processed to generate an image of the tissue or object in a region of interest. The resulting image is usually referred to as a B-scan image.

Measuring and imaging tissue motion and blood flow within a living body is typically done using the Doppler principle, in which a transmitted burst of ultrasound pulses at a specific frequency is reflected from the moving tissue, thereby changing the frequency of the reflected ultrasonic wave in accordance with the velocity and direction of tissue motion. The Doppler frequency shift of reflected signals with respect to the transmitted signals is proportional to the velocity of tissue motion. The mean frequency shift and its amplitude at each Doppler sampling location may be detected and displayed on a video device to provide graphic images of moving tissue or fluid flow within a living body.

The detection and identification of tumors, in particular, are often accomplished during real-time interactive ultrasonic imaging of internal tissues. Manual compression of internal tissues by applying pressure on the ultrasonic transducer probe through the skin may provide useful information about the elasticity or softness of various components of internal organs as the operator observes how the various components respond to applied manual pressure (changing shape, sliding, rolling, etc.).

The use of mechanical vibration at an audio frequency may reduce the variability of the magnitude and rate of compression while preserving freehand scanning in a lightweight hand-held probe. The vibration is continuous, and the vibrational source is controlled by well-defined control settings—frequency, output power, waveform, etc. This method combines separate ultrasound and audio transducers to send vibrations into a living body and ultrasonically detect the induced tissue vibrations using the Doppler principle. A transmitted burst of ultrasound at a specific frequency is reflected from moving tissue, changing the frequency of the reflected ultrasound in accordance with the velocity and direction of tissue vibration. The Doppler frequency shift of reflected signals with respect to the transmitted signals is proportional to the velocity of tissue motion. Whenever this frequency exceeds a low-frequency noise threshold, its amplitude or variance may be detected and displayed on a video display device to provide graphic images of moving tissue structure within a living body on the basis of its vibrational properties.

Present ultrasonic tissue motion imaging techniques include frequency-shift color Doppler imaging (CDI), power color Doppler imaging, and variance color Doppler imaging of tissue motion, as well as cross-correlation ultrasound estimation of displacements and mean velocities (such as color velocity imaging, or CVI, developed by Philips Corporation, and elastographic imaging techniques as developed by the University of Texas). These present known methods of ultrasound tissue motion imaging provide relatively limited information regarding the physical properties and direction of motion in a complex medium or a living body. For example, present CDI techniques primarily provide the frequency-shift that is dependent on both the velocity of tissue motion or fluid flow and the Doppler angle between the ultrasound beam and the direction of motion or flow. They may also provide the amplitude of Doppler signals that is dependent on the number and reflectivity of moving tissue reflectors. However, CDI techniques do not provide any information on the mechanical properties of living tissues. Cross-correlation techniques detect and display a limited range of velocities of motion or flow. Although cross-correlation methods can provide information on tissue elasticity and compressibility when viewed during application of an externally-applied mechanical stress, the algorithms involved are complex and computationally intensive, often involving acquisition of radio frequency (RF) data, thus requiring increased processing time and computer resources. Furthermore, because of the uncertainty in cross-correlation estimates of velocity and errors introduced by lateral decorrelation, the signal-to-noise ratio and spatial resolution of these methods have typically been limited. A related technique, vibrational Doppler imaging (VDI), provides elastographic information based on induced vibration at a given frequency and power color Doppler imaging of induced tissue motion. VDI provides improved spatial and contrast resolution as well as improved reproducibility of compression in a hand-held probe. Because VDI images contain a mixture of both acoustic reflectivity, tissue elasticity, and vibrational resonance information, they may be diagnostically ambiguous, depending on the chosen vibrational frequency.

The present invention, a vibrational resonance ultrasonic Doppler spectrometer, detects and differentiates embedded structures and tissues on the basis of vibrational resonance properties that may be affected by elasticity, size and mass of structural subunits, vibrational damping properties, etc. These mechanical properties may not be detectable or visible with most prior ultrasonic imaging methods. In a heterogeneous compressible medium, such as living tissue, vibrational resonance is observable in domains of locally more echogenic material (acoustic scatterers) which are elastically coupled through less echogenic tissues to other nearby domains as shown schematically in FIG. 7. The more echogenic scatterers matter only because they are the foci that provide the detectable Doppler echoes upon which vibrational resonance spectrometry and imaging are based. In addition, the vibrational resonance ultrasonic Doppler imager displays the spatial distribution of these properties in a two-dimensional imaging slice of the medium or tissue.

Because vibrational resonance ultrasonic Doppler spectrometry and imaging both utilize an entire range of vibrational frequencies, much greater information on the mechanical properties of various compressible media or soft tissues is acquired with which to differentiate them on the basis of a vibrational resonance "signature". This provides potentially improved sensitivity and specificity over previous ultrasound imaging techniques, including VDI, and may be particularly useful in detecting and differentiating tumors in soft organs such as the breast, prostate, and liver.

SUMMARY OF THE INVENTION

A system is described for identifying diverse soft structures in a complex compressible medium or soft tissues in a living body according to their characteristic vibrational resonance spectra. A system is further described for performing ultrasonic imaging of the vibrational resonance properties of heterogeneous media or soft biological tissues. A variable-frequency source of mechanical vibration is externally applied to a complex medium or living body to induce vibrations in various internal structures. As the externally-applied vibration is stepped incrementally through a range of vibrational frequencies, the resulting vibrational resonance amplitude is measured by power color Doppler imaging means. This vibrational resonance spectrum provides a characteristic curve for any echogenic soft structure within a complex compressible medium or any echogenic soft tissue within a living body.

In one embodiment of the present invention, the vibrational resonance ultrasonic Doppler spectrometer, the vibrational resonance spectrum is displayed for a graphically-defined region of interest. In an alternative embodiment of the present invention, the vibrational resonance ultrasonic Doppler imager, vibrational resonance spectra are acquired at each of a plurality of locations in an image, curve shape criteria are applied to differentiate the vibrational resonance characteristics at each location, and the resulting values are mapped into different colors in a two-dimensional space to provide a vibrational resonance image.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which.

DETAILED DESCRIPTION OF THE PREFERRED EMBODIMENTS

Figure 1:
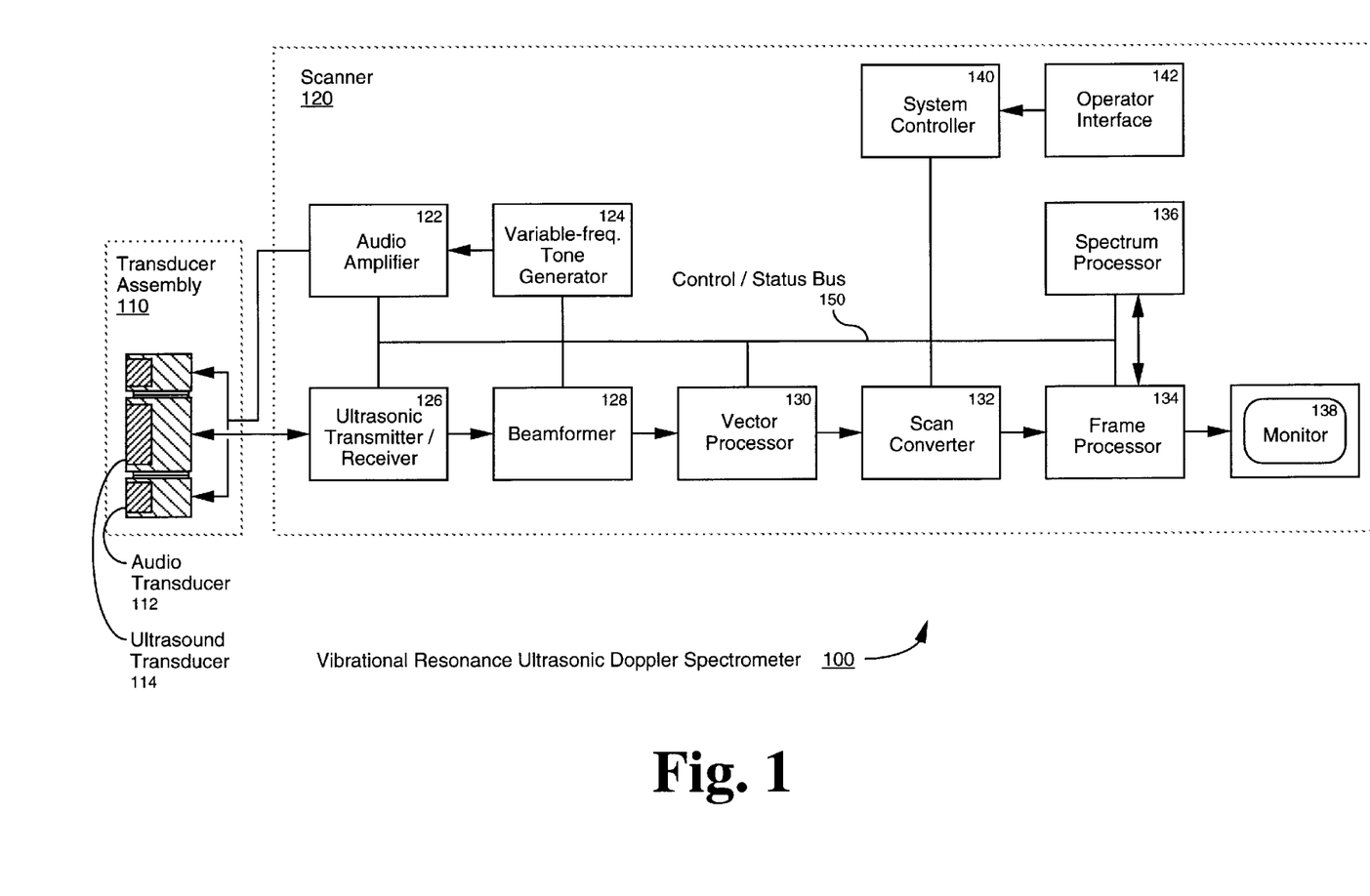
FIG. 1 is a block diagram of an ultrasonic imaging system that incorporates embodiments of the present invention.

An ultrasonic imaging apparatus shown in FIG. 1 comprises an ultrasound transducer 114 coupled to an ultrasound scanner. The ultrasound scanner comprises a transmitter/receiver 126 which generates electronically-focused transmit pulses to be sent through multiple channels to the ultrasound transducer. Echoes are received through the ultrasound transducer in multiple channels and electronically focused in the beamformer 128 to optimize the signal-to-noise ratio for echoes from a specific depth and lateral position in the medium or body. After summation into a single signal, the vector processor 130 performs RF processing, demodulation, Doppler processing, various bandpass and noise filtering, and clutter elimination. The scan converter 132 transforms vector coordinates (based on transducer geometry and electronic steering of ultrasound beams) into the Cartesian coordinates of a raster display device. The frame processor 134 accumulates image frame data; stores multiple frames for temporal averaging, compounding, three-dimensional image reconstruction, etc.; assigns gray-scale levels and colors to individual pixels; and adds overlay graphics before display on the monitor 138. All elements of the ultrasound scanner are digitally controlled through the control/status bus 150 by the system controller 140 with attached operator interface 142.

A vibrational resonance ultrasonic Doppler spectrometer is further illustrated in FIG. 1 comprising in addition a variable-frequency tone generator 124 whose waveform is amplified by an audio amplifier 122 before being sent to the audio transducer(s) 112 in the transducer assembly 110. The tones are of sufficient amplitude to induce palpable vibrations in the medium or tissue, which can be detected by a conventional ultrasonic power color Doppler imaging apparatus. Under control of the system controller, the tone generator steps through a cycle of frequencies in order to sweep through a specified vibrational resonance frequency range. Each frequency step is held for approximately 3–10 seconds, depending on the maximum duration required for stabilization of a vibrational resonance at a given stimulus frequency. The 10–40 frequency steps are logarithmically distributed from 10 Hz to, say, 350 Hz to generate a useful spectrum of vibrational resonance data points. Typically under software control, the system controller preselects the audio stimulus frequency range, number of frequency steps, step durations, audio signal waveform (square, sawtooth, sine, etc.), and audio output power at each step. These parameters are displayed on the image screen for documentation of device settings. A spectrum processor 136 uses power color Doppler imaging data in the frame processor 134 to generate vibrational resonance spectra. In a first embodiment of the present invention, this spectrum is graphically represented in the frame processor 134 for display on the monitor 138. In an alternative embodiment of the present invention, vibrational resonance spectra are generated for each of a plurality of sample volumes, assigned colors according to specific curve shape criteria, and represented as a two-dimensional color and/or brightness image.

By bouncing focused ultrasonic waves off of volume elements within the medium, Doppler signal processing detects frequency shifts in the returning echoes from moving acoustic reflectors within each volume element. Whenever a frequency shift is detected above a given threshold frequency (high-pass filter generally set just above the low-frequency noise floor), coherent motion is detected. Because frequency shifts alternate between positive and negative Doppler shifts at the rate of the vibrational source, the temporally-averaged frequency shift signal largely cancels itself out, leaving only noise. That leaves the Doppler variance signal which is a measure of the generally random spread of Doppler shifts. On the other hand, the Doppler amplitude signal is a measure of the fractional volume of acoustic reflectors exceeding the given threshold Doppler shift and the magnitude of the strain displacement. These yield a vibrational resonance spectrum when the vibrational source steps through a range of audio frequencies.

The amplitude is also proportional to the density and echogenicity of moving acoustic reflectors per volume element, and inversely related to attenuation in the intervening medium. Hence, a pure power Doppler image of induced vibrations (such as VDI) exhibits a "contaminating" echogenicity component in addition to the vibrational strain displacement and resonance components. The vibrational resonance ultrasonic Doppler spectrometer overcomes this by looking at Doppler amplitude variation as a function of vibrational stimulus frequency with the potential to subtract out the relatively frequency-invariant echogenicity component. This provides a highly specific vibrational resonance spectral "signature" curve for the material or tissue being imaged.

Transducer

Figure 2:
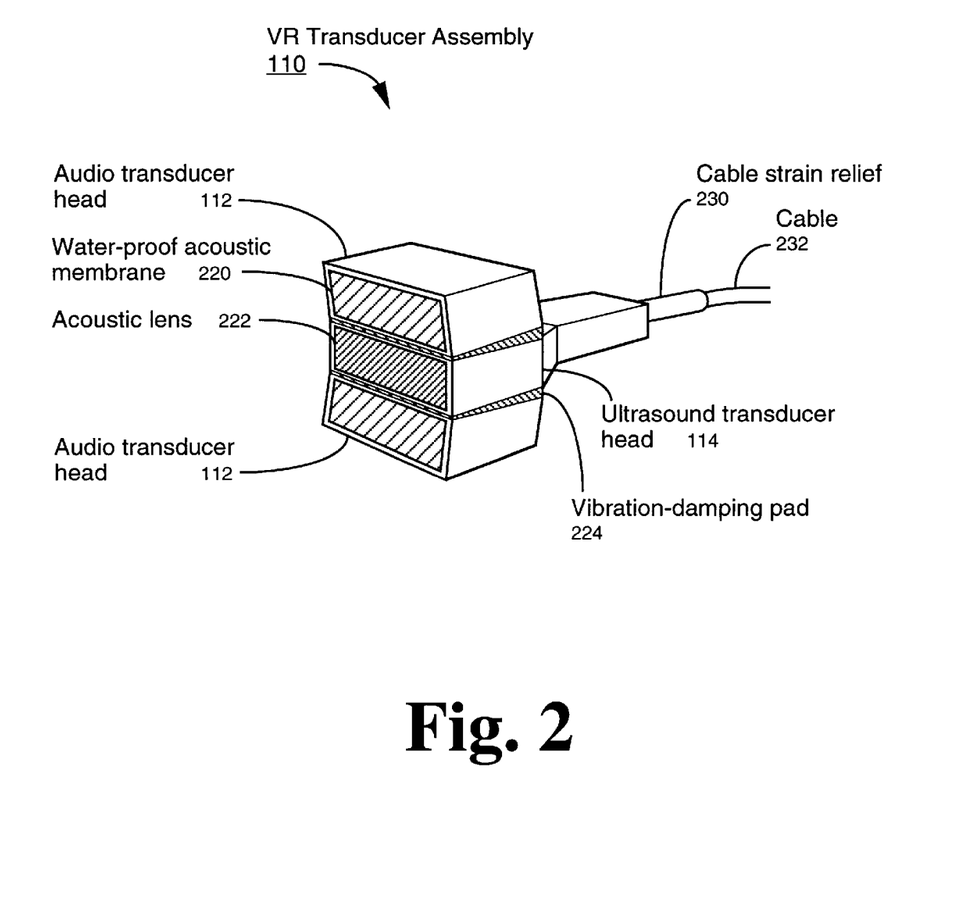
FIG. 2 illustrates an exemplary probe consisting of an ultrasound transducer and two fixed audio transducer heads, according to one embodiment of the present invention.

The vibrational resonance transducer assembly shown in FIG. 2 comprises an ultrasound transducer 114 and attached audio transducer(s) 112—one, or preferably two for elevational symmetry. Each audio transducer is attached to an elevational side of the ultrasound transducer through a vibration-absorbing pad 224. The angle of attachment is fixed at a low angle to direct vibrational waves towards a practical mid-field of the plane of ultrasonic imaging. The face of the vibrational resonance transducer assembly then comprises an acoustic lens 222 over the ultrasound transducer and water-proof acoustic membranes 220 over the audio transducers. All transducers are coupled to the vibrational resonance ultrasonic Doppler scanner by means of a cable 232, protected by a cable strain relief 230.

Figure 3:
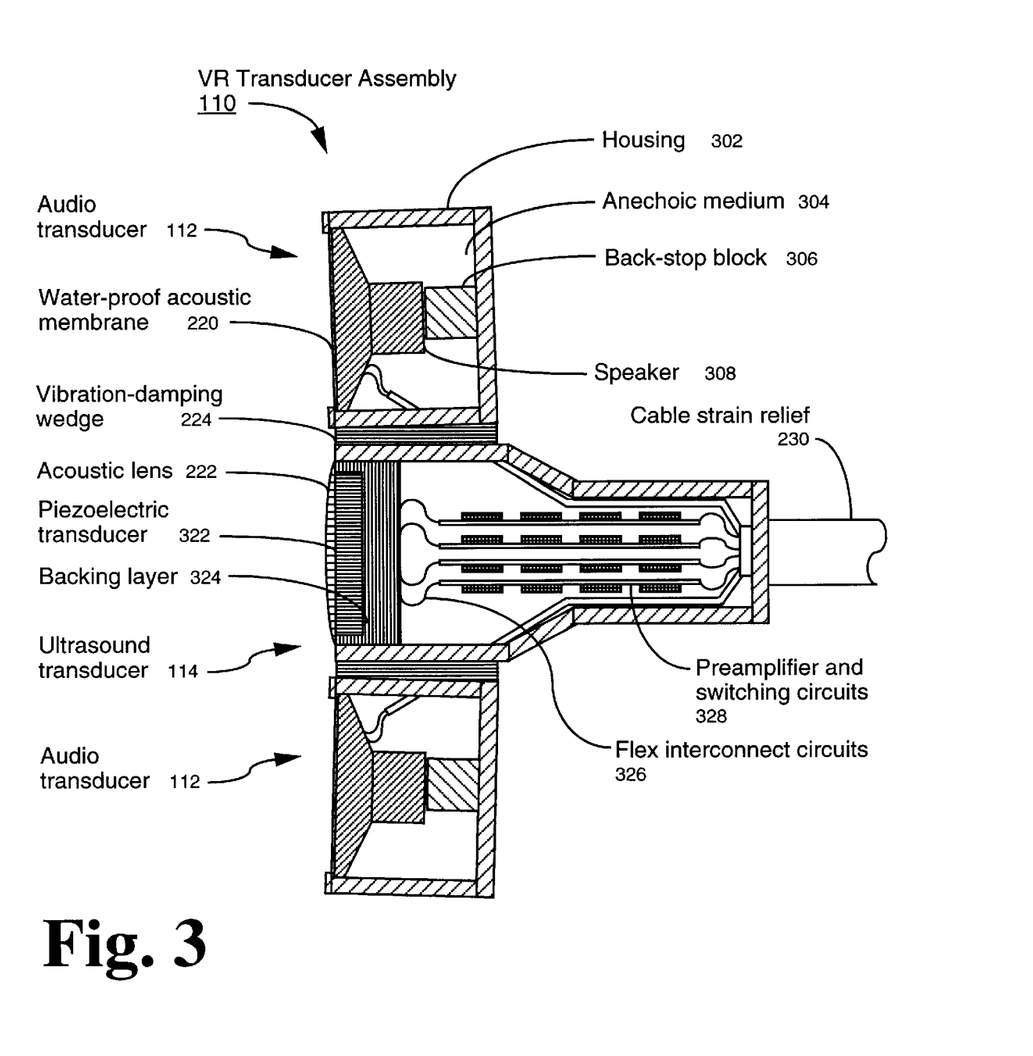
FIG. 3 illustrates a cut-away view of an exemplary probe consisting of an ultrasound transducer and two fixed audio transducer heads, according to one embodiment of the present invention.

Additional detail of the vibrational resonance transducer assembly is illustrated in the cut-away view of FIG. 3. The entire ultrasound transducer 114 is seen in cross-section, comprising the acoustic lens 222, piezoelectric transducer 322, acoustic-dampening backing layer 324, flex interconnect circuits 326 to each transducer element, exemplary preamplifier and switching circuits 328, and cable strain relief 230. Each audio transducer 112 is comprised of a housing 302, water-proof acoustic membrane 220, audio transducer element 308 (e.g., small loudspeaker or piezoelectric device), anechoic medium 304 (e.g., sound-absorbing foam), and any of a variety of mounting schemes (e.g., back-stop block 306).

Although the present invention is discussed with reference to specific embodiments, it can be appreciated by one skilled in the art that these are for illustrative purposes only, and are not intended to limit the scope of and subject matter of the present invention. It can be appreciated by one skilled in the art that many modifications may be made without departing from the overall spirit and scope of the present invention.

Vibrational Resonance

Figure 4:
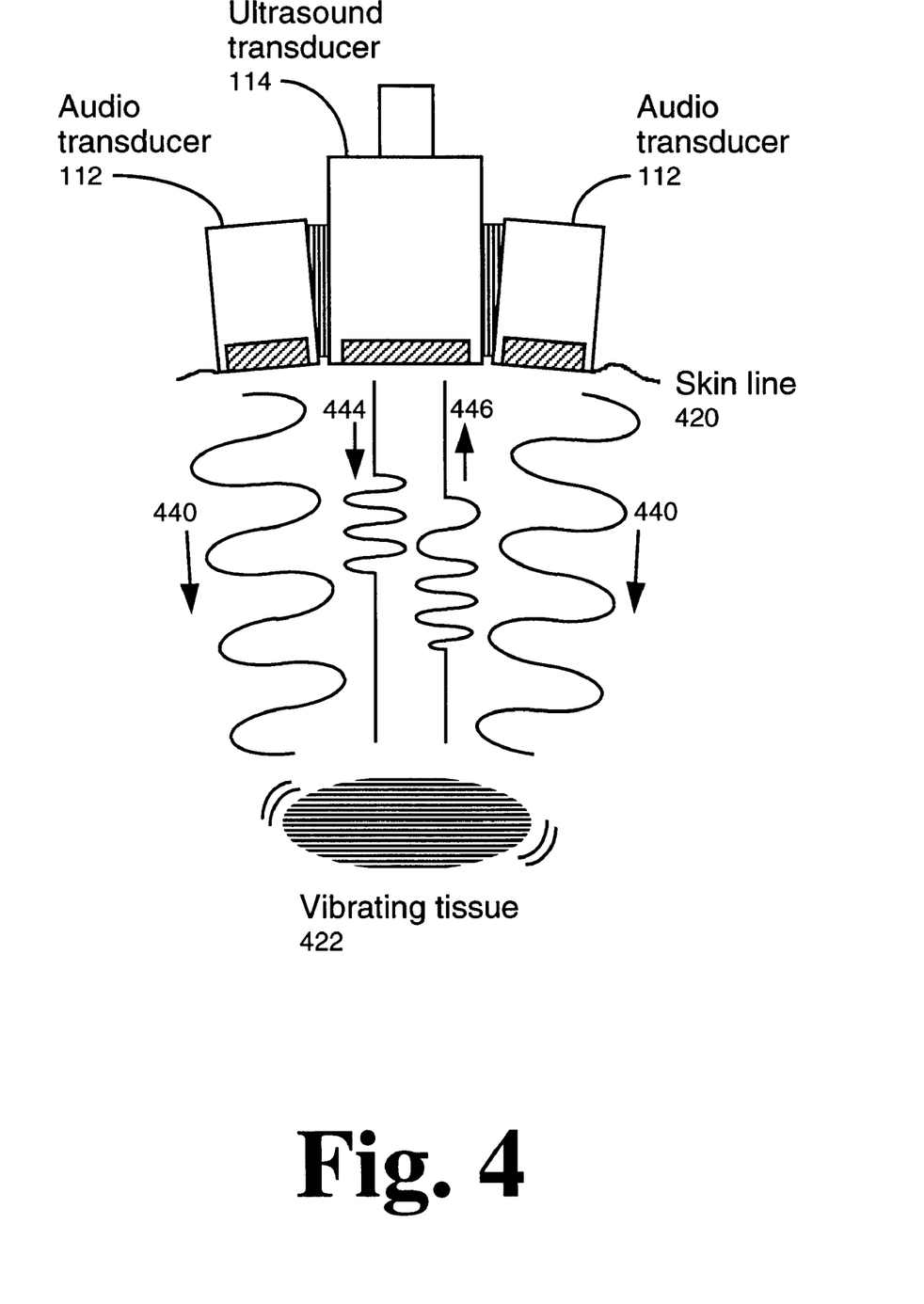
FIG. 4 illustrates two audio transducers applying a continuous wave vibrational stimulus to a body, an embedded soft tissue structure being induced to vibrate, an ultrasonic transducer transmitting a pulsed Doppler beam into the body, and a frequency-shifted Doppler echo from the soft tissue structure returning to the ultrasound transducer.

The basic physical set-up is shown in FIG. 4 in which a vibrational resonance transducer assembly is placed on a living body. The audio transducers 112 placed on the skin line 420 send continuous vibrational waves 440 into the body, stimulating a vibrational response in embedded tissue 422. Meanwhile, the ultrasound transducer 114 transmits a pulsed Doppler beam 444 at a known frequency. The vibrating tissue causes Doppler frequency shifts in the reflected ultrasonic wave 446 relative to the transmitted frequency of ultrasonic wave 444. The returning echoes are received by the ultrasound transducer and sent to the ultrasound system, where the Doppler shifts are detected and processed.

Figure 5:
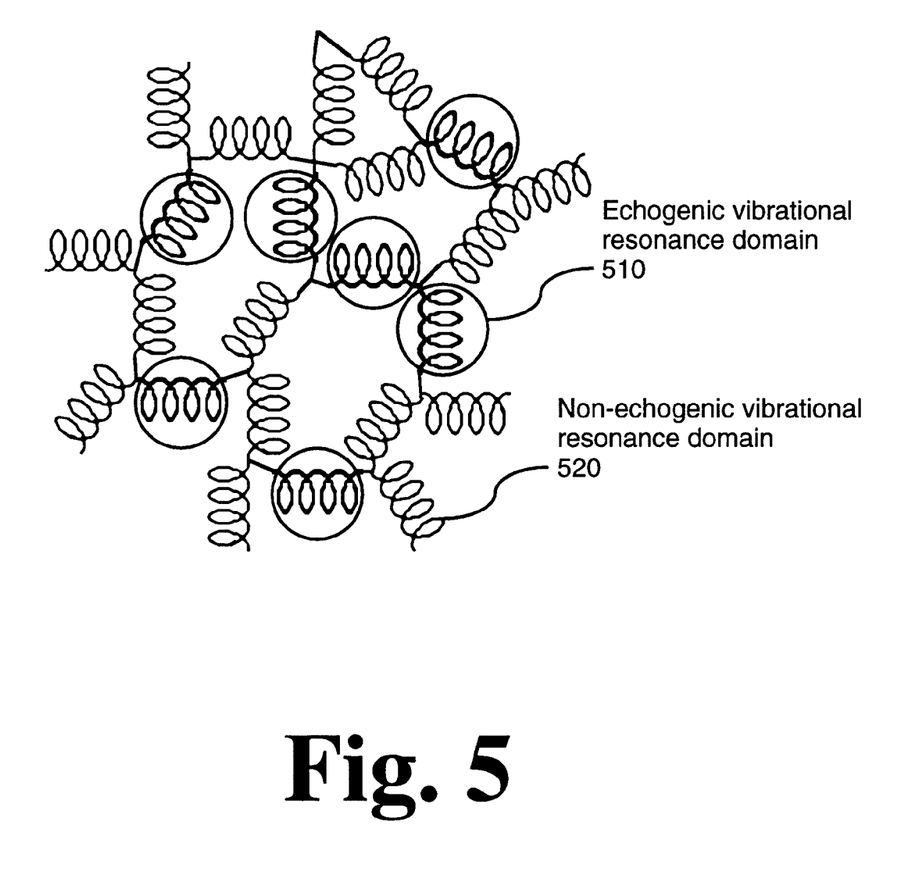
FIG. 5 illustrates a mechanical model of heterogeneous vibrational resonance domains.

Vibrational resonance is a property of all compressible materials. Homogeneous materials with simple geometric shapes may have one or more modes of harmonic oscillation, depending on the number of oscillatory degrees of freedom. Pure materials may have sharp (narrow bandwidth) resonances. Owing to the different mechanical properties of various materials, composite media are likely to have diffuse (wide bandwidth) resonances or multiple resonances. Heterogeneous media, such as biological tissues, are even more complex, and typically have multiple broad resonance peaks. In the audio frequency range, vibrational resonance in biological tissue takes place primarily in vibrational domains. Because vibrational resonance as detected by ultrasonic power color Doppler imaging is seen to rise in some domains as it falls in others when the audio frequency is incrementally changed, and these domains appear to be on the order of 0.3–3 millimeters across, the vibrational resonance phenomenon is observed in local domains in addition to any possible bulk resonance (normal modes of confined waves) of an organ, body part, or whole body. FIG. 5 illustrates a model of a heterogeneous medium comprised of vibrational domains as a network of randomly-connected springs. Each domain is a harmonic oscillator with an effective characteristic mass m and an aggregate elastic force contant k, whose resonant frequency f is given by:

$$f = \frac{1}{2\pi}\sqrt{\frac{k}{m}}.$$

While echogenic vibrational resonance domains 510 are more responsible for observable ultrasonic Doppler signals than non-echogenic vibrational resonance domains 520, the latter account for elastic media in between visualizable domains that contribute to the composite elastic force contants of echogenic domains.

Figure 6:
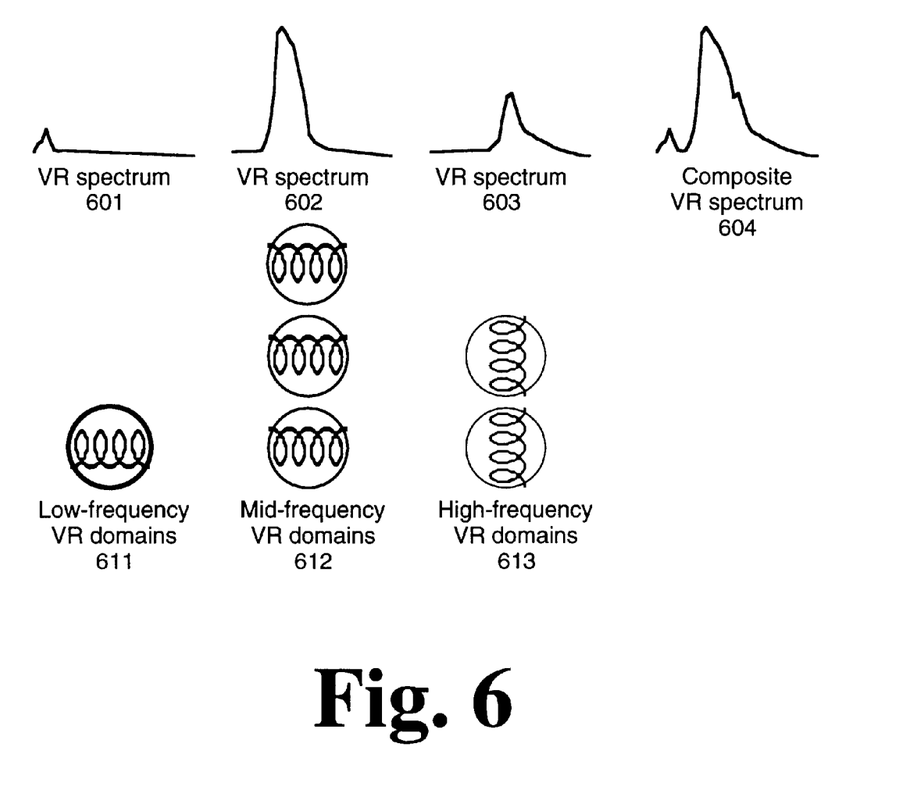
FIG. 6 illustrates vibrational domains of different resonant frequencies contributing individual resonance peaks to a composite vibrational resonance spectrum.

FIG. 6 illustrates how a low-frequency vibrational resonance domain 611 may give rise to a low-frequency resonant peak 601. A high density of echogenic mid-frequency vibrational resonance domains 612 may generate a comparatively high-amplitude resonance peak 602, and so on. Adding together the contributions of all types of vibrational resonance domains yields a composite multi-peak vibrational resonance spectrum 604. In this manner, a vibrational resonance spectrum provides a "signature" of the vibrational resonance properties of the various constituent domains in a complex compressible medium or in a living body.

Sequencing of Vibrational and Ultrasonic Imaging Functions

Figure 7:
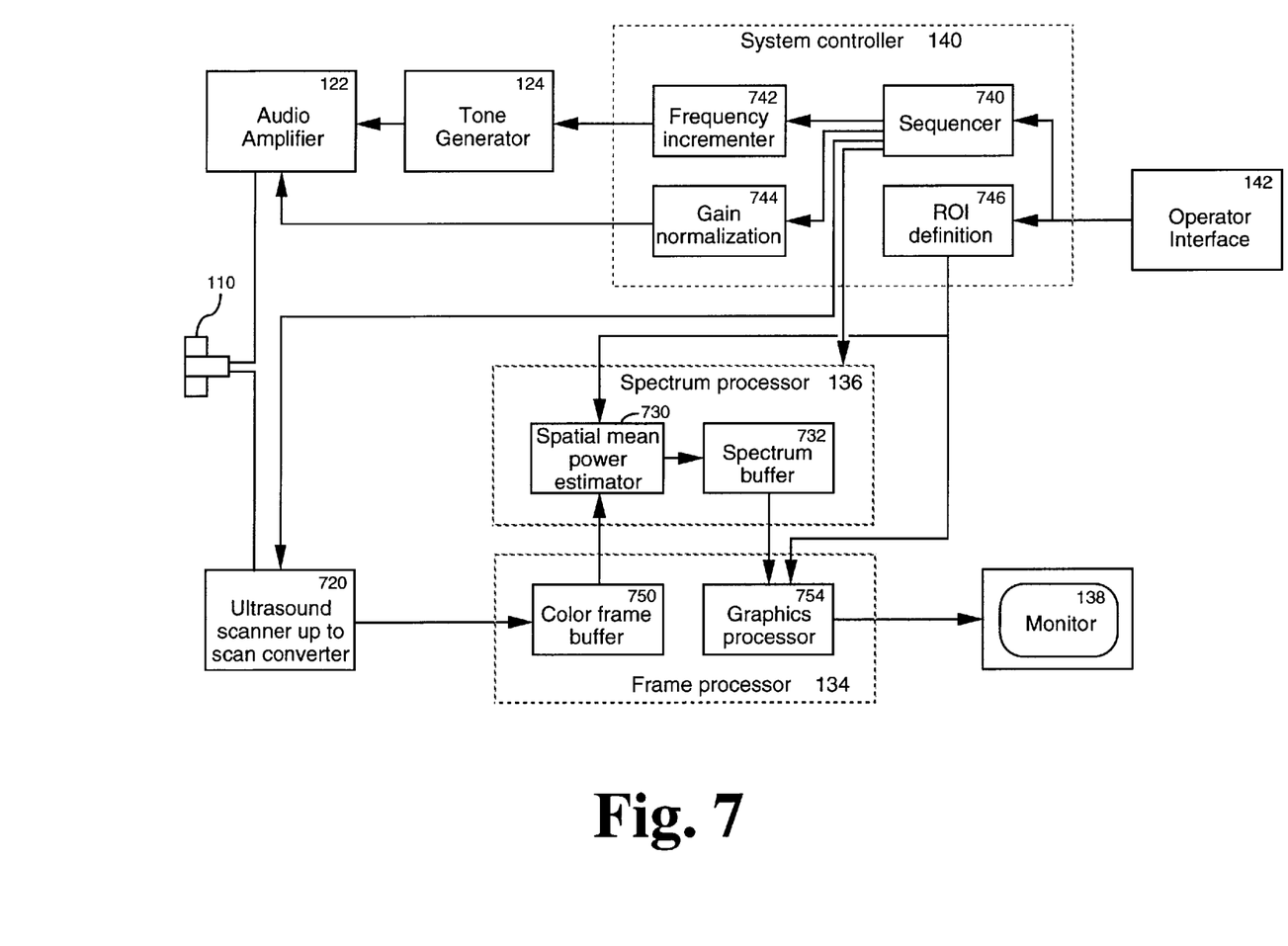
FIG. 7 is a block diagram of the circuitry for synchronizing audio-frequency vibrations with ultrasonic Doppler data acquisition and processing for vibrational resonance spectrometry, according to one embodiment of the present invention.

In one embodiment of the present invention, the major functional subunits of an ultrasonic imaging apparatus uniquely required to perform vibrational resonance ultrasonic Doppler spectrometry are shown in FIG. 7. The system controller 140 comprises a sequencer 740 which provides timing information to other subunits to coordinate tone generation through a vibrational frequency range and spectrum acquisition. The sequencer is one of a plurality of functional subunits in the system controller which receives instructions from the operator interface 142. The sequencer tells the frequency incrementer 742 when to step to the next frequency which, in turn, specifies a new frequency to the tone generator 124. At the same time, the sequencer tells the gain normalization algorithm 744 to adjust the gain of the audio amplifier 122 to normalize audio output power at probe 110 for the next frequency. The ultrasound transducer in probe 110 and ultrasound scanner 720 are operated in the conventional manner for power Doppler imaging, except that Doppler gain and pulse repetition frequency are typically lower than for blood flow imaging. The scan-converted power Doppler image is assembled in raster format in the color frame buffer 750. After allowing a predetermined amount of time for a resonance vibration to stabilize—typically 3–10 seconds in biological tissue—the sequencer initiates acquisition of a spectral data point. The operator has already graphically specified a region of interest (ROI) through the ROI definition algorithm 746. The spatial mean power estimator 730 computes the mean Doppler amplitude within the ROI in an image in the color frame buffer. This data point and those for all other vibrational frequencies are accumulated in the spectrum buffer 732 for graphical layout in the graphics processor 754 and display on the monitor 138.

Figure 8:
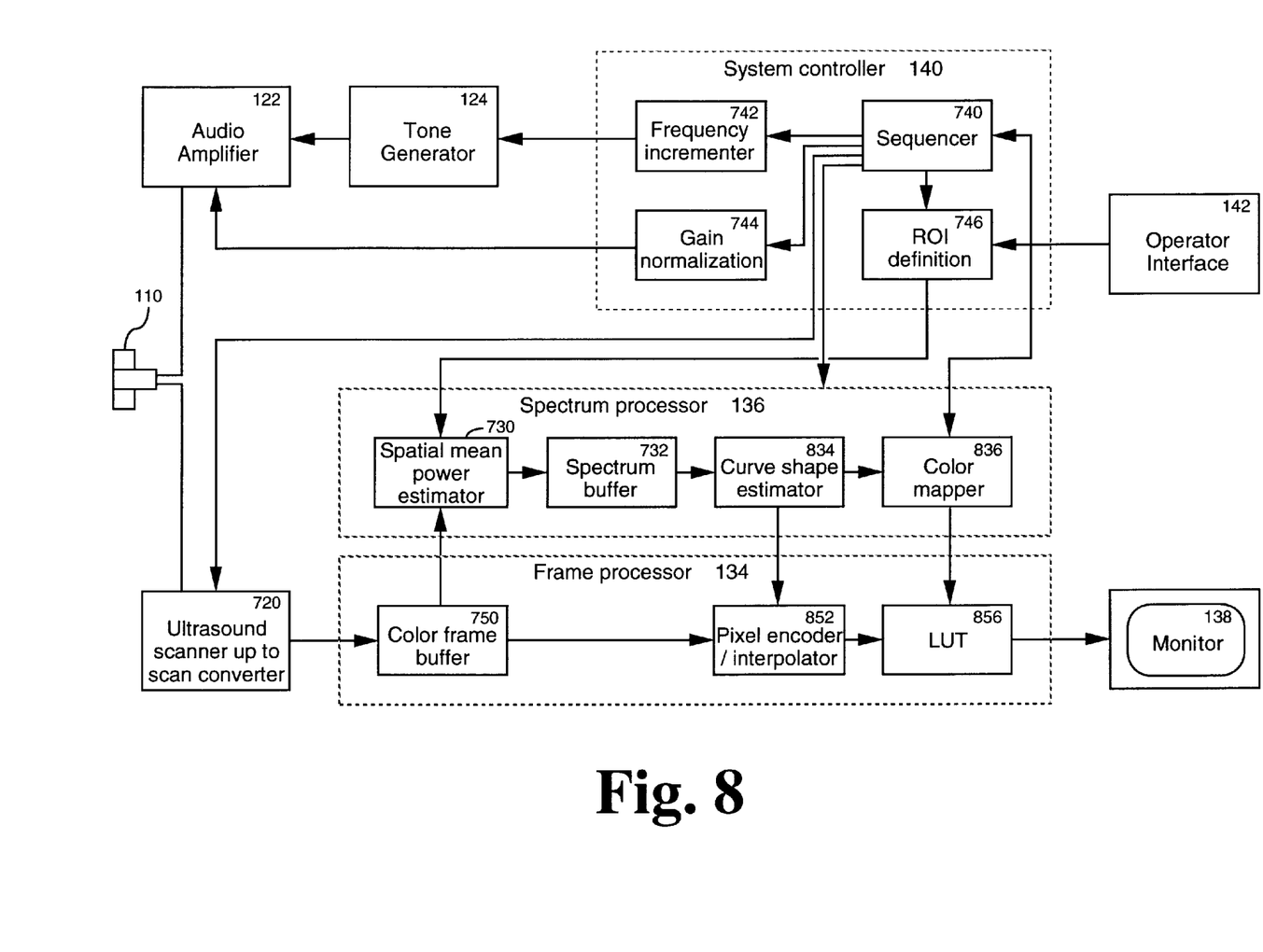
FIG. 8 is a block diagram of the circuitry for synchronizing audio-frequency vibrations with ultrasonic Doppler data acquisition and processing for vibrational resonance imaging, according to an alternative embodiment of the present invention.

In another embodiment of the present invention, the major functional subunits of an ultrasonic imaging apparatus uniquely required to perform vibrational resonance ultrasonic Doppler imaging are shown in FIG. 8. The sequencer 740 provides timing signals as described above to the frequency incrementer 742, gain normalization algorithm 744, and ultrasound scanner front end 720. The same operations are performed up to assembling the scan-converted power Doppler image in raster format in the color frame buffer 750. Following commands from the operator interface 142, the ROI definition algorithm 746 divides the color image into a two-dimensional matrix of n×n pixel ROIs (where n is typically 1–5, depending on trade-offs between spatial resolution and filtering). The spatial mean power estimator 730 computes the mean Doppler power in each ROI. The spectrum buffer 732 accumulates data points from each ROI for each respective spectrum. A spectrum consists of spatial mean Doppler power data at all vibrational resonance frequencies. The curve shape estimator 834 uses predefined curve shape criteria to generate the quantitative indices used by the pixel encoder/interpolator 852 to assign values to center pixels in each ROI in a vibrational resonance ultrasonic Doppler image. The pixel interpolator fills in pixel values in between neighboring center pixels. The color mapper 836, having previously received color mapping commands from the operator interface via the system controller, loads the look-up table (LUT) 856. Color window limits may be adjusted according to the ranges of index values generated by the curve shape estimator. Encoded values at each pixel in the vibrational resonance ultrasonic Doppler image are mapped into colors using the LUT, and displayed as a color image on the monitor 138.

Figure 9:
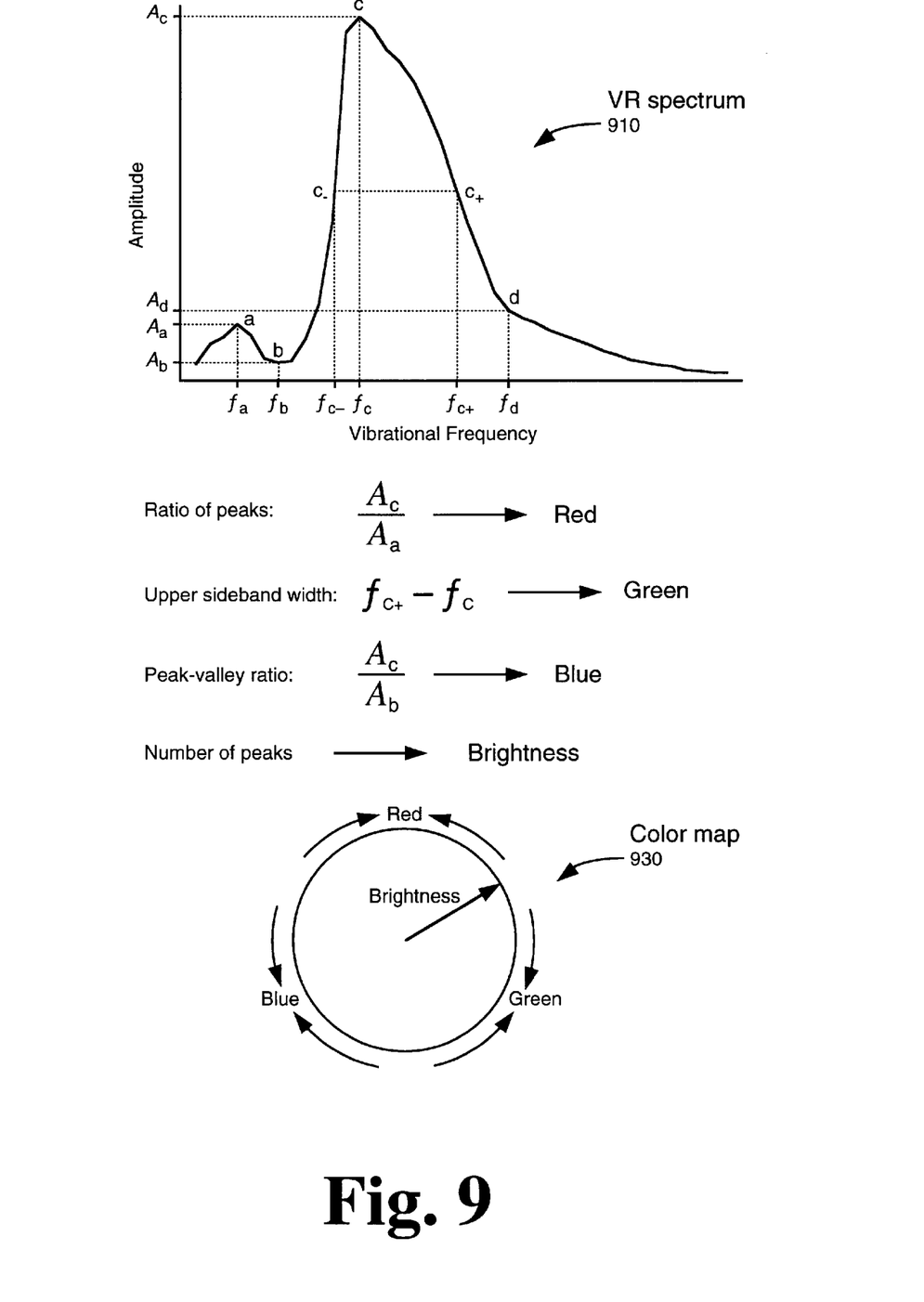
FIG. 9 illustrates how an exemplary set of curve shape criteria can be applied to a vibrational resonance spectrum to generate a color mapping, according to one embodiment of the present invention.

FIG. 9 illustrates a typical vibrational resonance spectrum 910 from living tissue, in which, exemplary spectral peaks a and c, −6 dB bandwidth points c− and c+ of the main peak, valley b, and a selected frequency point d are identified. On the basis of such features of the spectrum, curve shape criteria may be quantified in terms of various attenuation-independent parameters. Examples of curve shape criteria include amplitude ratios $$\frac{A_c}{A_a}$$

or $$\frac{A_c}{A_b},$$

frequency parameters such as peak location $f_c$ or upper sideband width $f_{c+}-f_c$, and number of peaks. Up to four quantities may be mapped into intensities of basic colors (red, green, and blue) and brightness, each combination defining a unique location on the color wheel 930.

Figure 10:
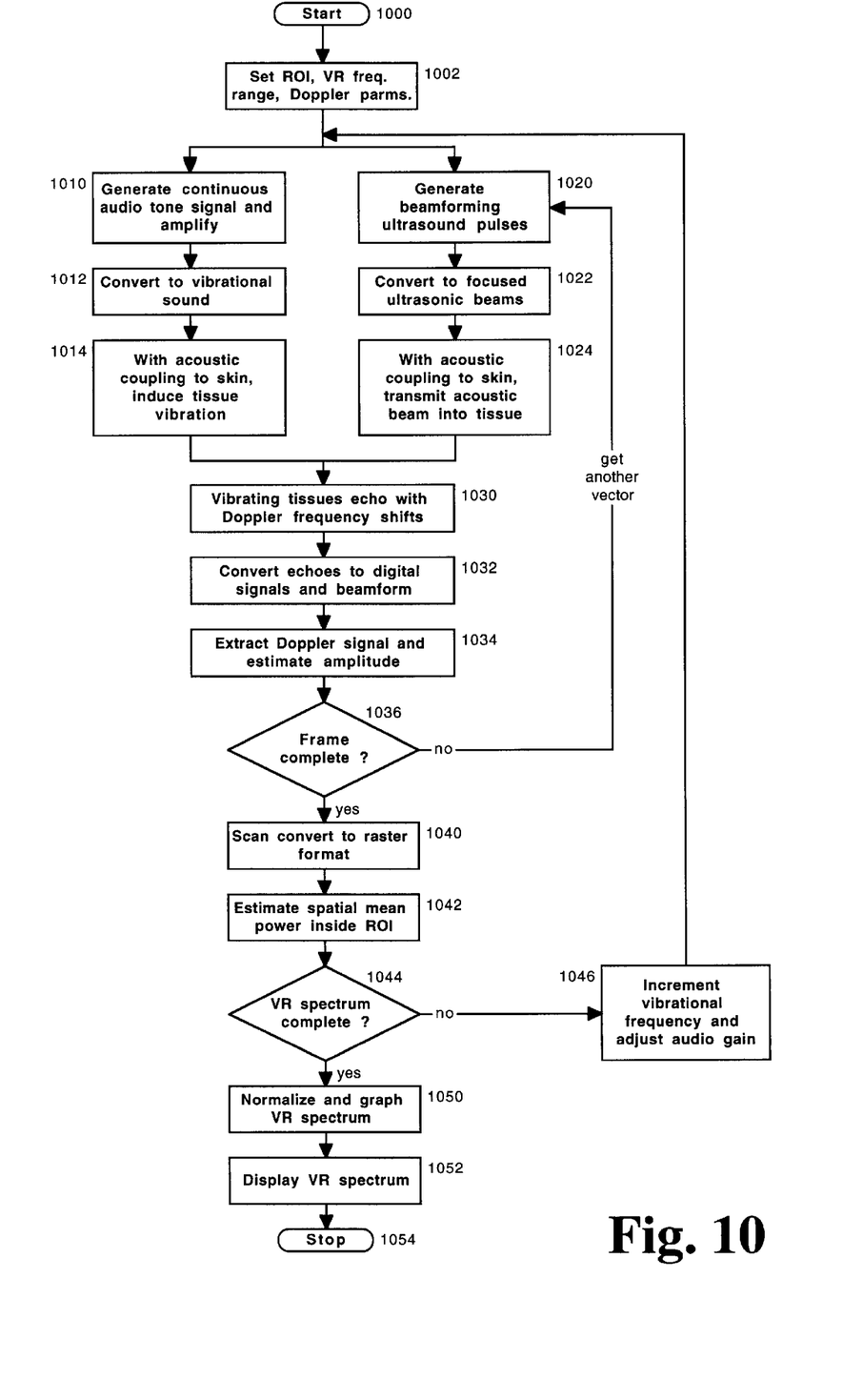
FIG. 10 is a flow chart illustrating the steps of performing vibrational resonance ultrasonic Doppler spectrometry according to one embodiment of the present invention.

The flowchart in FIG. 10 illustrates the steps of performing vibrational resonance ultrasonic Doppler spectrometry according to one embodiment of the present invention. In step 1002, operator settings are made for vibrational frequency range, vibrational frequency step intervals, ROI area, Doppler acquisition parameters, etc. Step 1010 begins the sequence of generating and amplifying an audio-frequency tone for conversion into a continuous vibrational wave (step 1012) and its transmission into a complex medium or living body (step 1014). After allowing sufficient time for a resonant vibration to stabilize, step 1020 begins a parallel sequence of generating and transmitting a focused ultrasonic pulsed Doppler beam into the complex medium or living body (steps 1022 and 1024). In step 1030, vibrating embedded structures or tissues reflect ultrasonic pulses with a Doppler shift proportional their instantaneous velocities. In step 1032, these echoes are converted to electric signals by the ultrasound transducer, digitized, and focused in the beamformer from a single sample volume. In step 1034, the summed signal is demodulated, and in-phase and quadrature signals are processed to obtain mean Doppler frequency shifts and amplitudes. The amplitudes of individual Doppler samples whose frequency shifts exceed a predefined high-pass filter threshold are stored. Vector acquisition is done by repeating the sequence, acquiring from successive sample volumes along each color Doppler vector from step 1020. Once the vectors for a complete color Doppler imaging frame have been acquired, the vector geometry is scan converted to raster format (Cartesian coordinates) in step 1040. In step 1042, the spatial mean Doppler amplitude is computed for the entire ROI and stored in the spectrum buffer. In step 1046, the vibrational stimulus frequency is incremented and the audio output level adjusted to compensate for variations in frequency response of the amplifier and audio transducer. Then the above sequence is repeated from steps 1010 and 1020. Upon cycling through all frequency steps in the specified vibrational frequency range, step 1050 normalizes the vibrational resonance spectrum to a scale or reference level and formats it into a graph. In step 1052, the vibrational resonance spectrum is displayed on the monitor.

Figure 11:
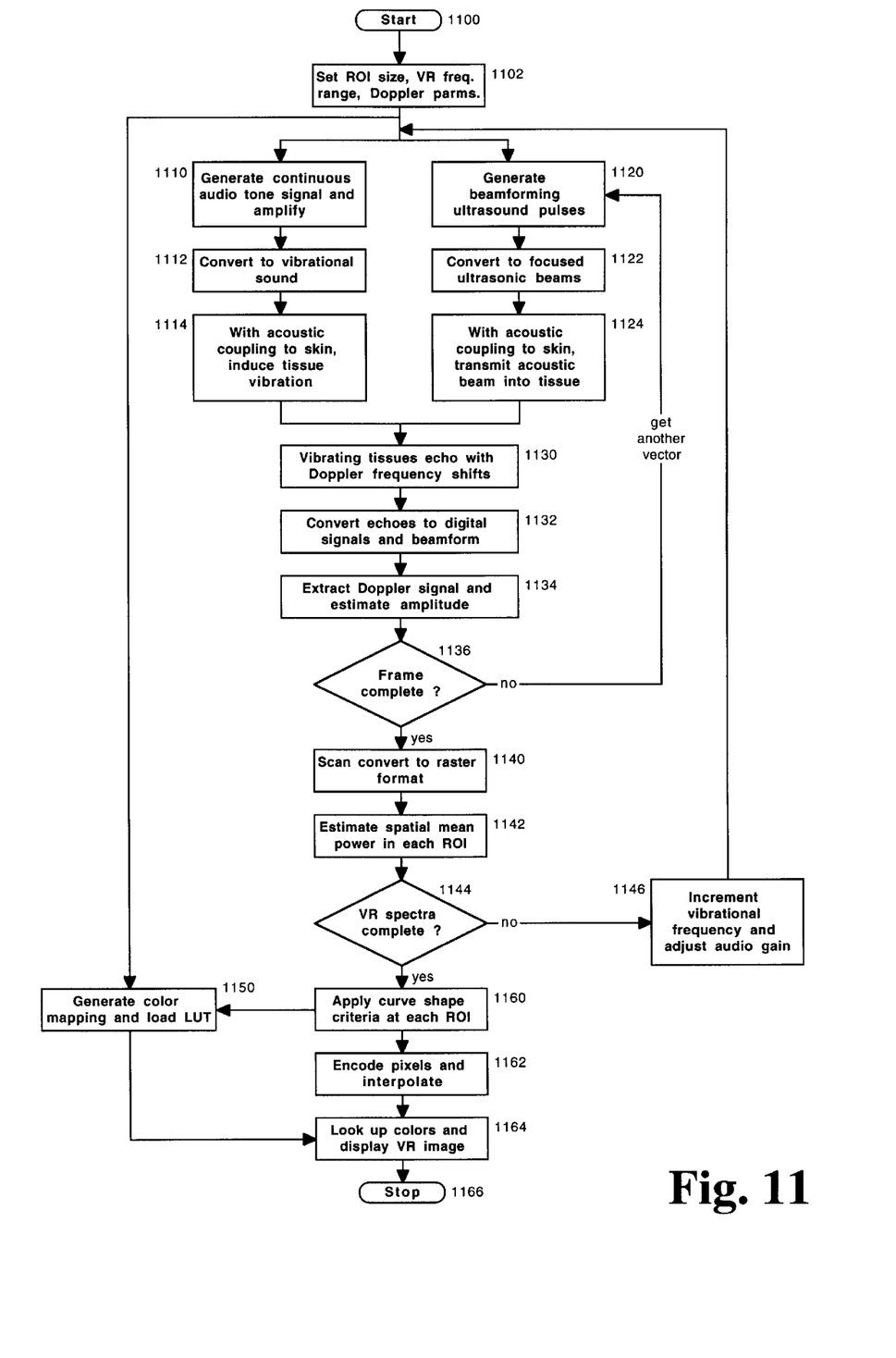
FIG. 11 is a flow chart illustrating the steps of performing vibrational resonance ultrasonic Doppler imaging according to an alternative embodiment of the present invention.

The flowchart in FIG. 11 illustrates the steps of performing vibrational resonance ultrasonic Doppler imaging according to an alternative embodiment of the present invention. In step 1102, operator settings are made for vibrational frequency range, vibrational frequency step intervals, ROI size, Doppler acquisition parameters, selection of curve shape criteria, color mapping scheme, etc. Steps 1110 and 1120 begin parallel sequences of vibrational stimulation and ultrasonic pulse transmission as described for FIG. 10. Step 1130 begins a sequence of power Doppler vector generation from echoes received from vibrating structures or tissues as described for FIG. 10. Color scan conversion is performed in step 1140. In step 1142, the spatial mean Doppler amplitude is computed for the each ROI and stored in the spectrum buffer—one additional data point for each vibrational resonance spectrum. In step 1046, the vibrational stimulus frequency is incremented and the audio output level adjusted to compensate for variations in frequency response of the amplifier and audio transducer. Then the above sequence is repeated from steps 1110 and 1120. Upon cycling through all frequency steps in the specified vibrational frequency range, step 1160 applies a set of curve shape criteria to the vibrational resonance spectrum to compute a set of characteristic indices. Step 1150 normalizes the previously-specified color maps to maximum index values, and loads the color look-up table (LUT). In step 1162, characteristic indices are encoded into pixels in the color frame buffer and two-dimensionally interpolated. In step 1164, pixels are assigned colors from the LUT, and the vibrational resonance image is displayed on the monitor.

In the foregoing, an ultrasound imaging system has been described for displaying the vibrational resonance spectrum of a region of interest in a medium or body. A system has been further described for displaying a vibrational resonance image of an area of a medium or body. Although the present invention has been described with reference to specific exemplary embodiments, it will be evident that various modifications and changes may be made to these embodiments without departing from the broader spirit and scope of the invention as set forth in these claims. Accordingly, the specification and drawings are to be regarded in an illustrative rather than a restrictive sense.

What is claimed is:

1. An ultrasonic imaging apparatus comprising:
    audio transducer(s) operable to transmit into a medium or body an audio-frequency vibrational tone, and wherein said audio transducer(s) cause embedded structures in said medium or body to vibrate at a plurality of resonant audio frequencies;
    an ultrasound transducer attached to said audio transducer(s) operable to transmit into said medium or body, a focused ultrasonic-frequency beam, and wherein said ultrasound transducer is further operable to receive from said medium or body reflected ultrasonic waves;
    a variable-frequency tone generator and amplifier coupled to said audio transducer(s) operable to sequentially generate a plurality of waveforms at incrementally higher frequencies within a range of audio frequencies;
    a frame processor coupled to said ultrasound transducer through the imaging pathway of said ultrasonic imaging apparatus, operable to buffer ultrasound image frames, assign colors and/or brightness to each pixel, and to overlay graphics;
    a spectrum processor coupled to said frame processor operable to estimate the vibrational resonance spectrum and/or vibrational resonance image of areas within said medium or body; and
    a system controller coupled to said variable-frequency tone generator, said amplifier, said frame processor, and said spectrum processor, operable to synchronize their functions to generate said vibrational resonance spectrum or said vibrational resonance image.

2. The ultrasonic imaging apparatus of claim 1 wherein:
    said audio transducer(s) consist of loudspeaker(s) or piezoelectric transducer(s) contained within housing (s);
    said housing(s) are attached at a fixed angle through vibration-absorbing pads to the elevational sides of said ultrasound transducer;
    a waterproof acoustic membrane seals an opening in said housing(s), provides a protective skin contact surface for said audio transducer(s), and is made of a material which allows transmission of audio sound waves therethrough; and
    said range of audio frequencies is within the range of 10 Hz to 1000 Hz.

3. The ultrasonic imaging apparatus of claim 1 wherein said spectrum processor is further comprised of:
    a spatial mean Doppler power estimator coupled to said frame processor operable to compute the mean Doppler power over a region of interest in the Doppler image; and
    a spectrum buffer coupled to said spatial mean Doppler power estimator, operable to accumulate data points at each vibrational frequency comprising said vibrational resonance spectrum.

4. The ultrasonic imaging apparatus of claim 3 wherein said spectrum processor is further comprised of:
    a curve shape estimator coupled to said spectrum buffer operable to apply curve shape criteria to quantify various identifying characteristics of said vibrational resonance spectrum; and
    a color mapper coupled to said curve shape estimator operable to set up color and brightness look-up tables for each said curve shape criterion for the purpose of color coding said vibrational resonance image.

5. The ultrasonic imaging apparatus of claim 4 wherein said curve shape estimator uses frequency and amplitude information in said vibrational resonance spectrum to locate spectral peaks and valleys, measure peak widths, calculate amplitude ratios, and count the number of said peaks.

6. The ultrasonic imaging apparatus of claim 4 further comprising:
    a transmitter/receiver coupled to said ultrasound transducer operable to transmit and receive a plurality of said focused ultrasonic-frequency beams;
    a beamformer coupled to said transmitter/receiver operable to focus on echoes received from a sequence of focal points within said medium or body;
    a vector processor coupled to said beamformer operable to estimate the Doppler frequency shift and amplitude of said echoes, and further operable to assemble a plurality of said Doppler frequency shifts and amplitudes along ultrasound vectors;
    a scan converter coupled to said vector processor operable to convert the geometric coordinate system of the ultrasound vectors into Cartesian coordinates (raster format);

a monitor coupled to said frame processor operable to display said vibrational resonance spectrum and/or said vibrational resonance image; and an operator interface coupled to said system controller operable to accept commands entered by an operator.

7. The ultrasonic imaging apparatus of claim 6 wherein said frame processor is further comprised of:

a color frame buffer coupled to said scan converter and to said spatial mean Doppler power estimator, operable to accumulate complete color image frames in raster format; and a graphics processor coupled to said system controller and to said spectrum buffer, operable to layout a graphical outline of one or more regions of interest in said color image frame, and further operable to graph said vibrational resonance spectrum.

8. The ultrasonic imaging apparatus of claim 7 wherein said frame processor is further comprised of:

a pixel encoder/interpolator coupled to said color frame buffer and to said curve shape estimator, operable to enter curve shape criterion indices into center pixels of each said region of interest, and further operable to interpolate said indices for pixels lying in between said center pixels; and a look-up table coupled to said color mapper and to said pixel encoder/interpolator, operable to define colors and brightness for said curve shape criterion indices in each said pixel.

9. A method of performing ultrasonic imaging of vibrational resonance comprising the steps of:

(a) generating and amplifying a sequence of waveforms incrementally stepped through a plurality of audio frequencies;

(b) converting said waveforms into vibrational tones;

(c) introducing said vibrational tones into an area of a medium or body to be ultrasonically imaged such that structures or tissues within said area are caused to vibrate at frequencies related to said vibrational tones;

(d) generating pulses at a fixed ultrasonic frequency;

(e) converting said pulses collectively into focused ultrasonic beams;

(f) introducing said focused ultrasonic beams into said area;

(g) receiving echoes from said area to estimate their mean Doppler power; and (h) assembling a vibrational resonance spectrum from said mean Doppler power over said plurality of audio frequencies in each region of interest within said area.

10. A method according to claim 9 wherein steps (a) through (c) are performed concurrently with steps (d) through (h).

11. A method according to claim 9 wherein:

said sequence of waveforms is introduced into said area through audio transducers coupled to a variable-frequency tone generator;

said focused ultrasonic beams are introduced into said area through an ultrasound transducer coupled to an ultrasonic Doppler imaging system; and said sequence of waveforms and said focused ultrasonic beams are synchronized by a common system controller.

12. A method according to claim 9 wherein said step of receiving said echoes to estimate their mean Doppler power comprises the steps of:

converting echoes of said focused ultrasonic beams from said area into electronic pulses;

beamforming said electronic pulses to focus on said echoes received from specific depths;

estimating Doppler frequency shifts and/or amplitudes, and filtering out echoes with said Doppler frequency shifts below a specified high pass frequency;

scan converting the resulting Doppler vector data into raster format; and estimating the mean Doppler power within each region of interest.

13. A method according to claim 9 further comprising the steps of:

(i) graphing said vibrational resonance spectrum; and (j) displaying said vibrational resonance spectrum.

14. A method according to claim 9 further comprising the steps of:

(k) applying curve shape criteria to each said vibrational resonance spectrum to quantify indices for each said region of interest;

(l) encoding said indices into center pixels in each said region of interest and interpolating indices for pixels in between said center pixels;

(m) mapping said pixels into colors and brightness; and (n) displaying the resulting vibrational resonance image.

15. A method according to claim 14 wherein said step of applying curve shape criteria comprises the use of frequency and amplitude information in said vibrational resonance spectrum for locating spectral peaks and valleys, measuring peak widths, calculating amplitude ratios, and counting the number of said peaks in order to compute a set of said indices.

16. An apparatus comprising:

audio transducer means for transmitting acoustic energy of a first set of audio frequencies into an area of a subject to be scanned;

ultrasound transducer means for transmitting acoustic energy of a second set of ultrasonic frequencies into said area, said ultrasound transducer means coupled to said audio transducer means;

variable-frequency tone generator means for synthesizing a sequence of waveforms at said first set of audio frequencies;

power Doppler processing means for estimating Doppler frequency shifts and amplitudes;

spatial mean Doppler power estimation means for quantifying vibrational resonance responses in said area of said subject;

spectrum buffer means for accumulating vibrational resonance spectra as said variable-frequency tone generator means sweeps through said first set of audio frequencies; and spectrum processor means for computing the vibrational resonance spectra of said area of said subject.

17. The apparatus of claim 16 further comprising attachment means for holding said audio transducer means at a fixed angle to the elevational sides of said ultrasound transducer means such that said audio transducer means and said ultrasound transducer means can be held in proximate contact with said area, and further such that vibration-absorbing pads mechanically insulate said ultrasound transducer means from the vibrations of said audio transducer means.

18. The apparatus of claim 16 further comprising:

graphical means for graphically formatting said vibrational resonance spectrum; and display means for displaying said vibrational resonance spectrum.

19. The apparatus of claim 16 further comprising:

curve shape characterization means for quantifying indices of vibrational resonance spectral "signature" characteristics;

pixel encoding means for assigning said curve shape characterization indices to pixels of a vibrational resonance image;

color mapping means for assigning colors and brightness to pixels of said vibrational resonance image; and display means for displaying said vibrational resonance image.

* * * * *